United States Patent [19]

Chai

[11] 4,291,694

[45] Sep. 29, 1981

[54] APPARATUS AND METHOD FOR PERFORMING A THORACIC OPERATION

[76] Inventor: S. Chai, 187 Bolivar La., Portola Valley, Calif. 94025

[21] Appl. No.: 89,221

[22] Filed: Oct. 29, 1979

[51] Int. Cl.³ ............................................. D61M 5/00
[52] U.S. Cl. .................. 128/214.4; 128/347; 128/350 R
[58] Field of Search ............... 128/347, 348, 349, 350, 128/214 R, 214.4

[56] References Cited

U.S. PATENT DOCUMENTS

| | | | |
|---|---|---|---|
| 1,527,291 | 2/1925 | Zorraquin | 128/347 X |
| 2,001,638 | 5/1935 | Tornsjo | 128/347 |
| 3,176,690 | 4/1965 | H'Doubler | 128/214 R X |
| 3,545,443 | 12/1970 | Ansari | 128/348 |
| 3,568,673 | 3/1971 | Cowley | 128/214.4 |
| 3,633,579 | 1/1972 | Alley et al. | 128/214.4 |
| 3,677,244 | 7/1972 | Hassinger | 128/214.4 |
| 3,840,008 | 10/1974 | Noiles | 128/214.4 X |
| 3,921,631 | 11/1975 | Thompson | 128/214.4 |

OTHER PUBLICATIONS

*Pye's Surgical Handicraft,* 16th Edition, 1950, p. 225, lines 6-30.

*Primary Examiner*—Stephen C. Pellegrino
*Attorney, Agent, or Firm*—Flehr, Hohbach, Test, Albritton & Herbert

[57] ABSTRACT

A kit of instruments including a hollow needle, a hollow pneumotube, and a cover assembly adapted for use in performing a percutaneous thoracic operation on a patient, and a method for performing a percutaneous pneumotube insertion in a patient with a documented pneumothorax.

12 Claims, 16 Drawing Figures

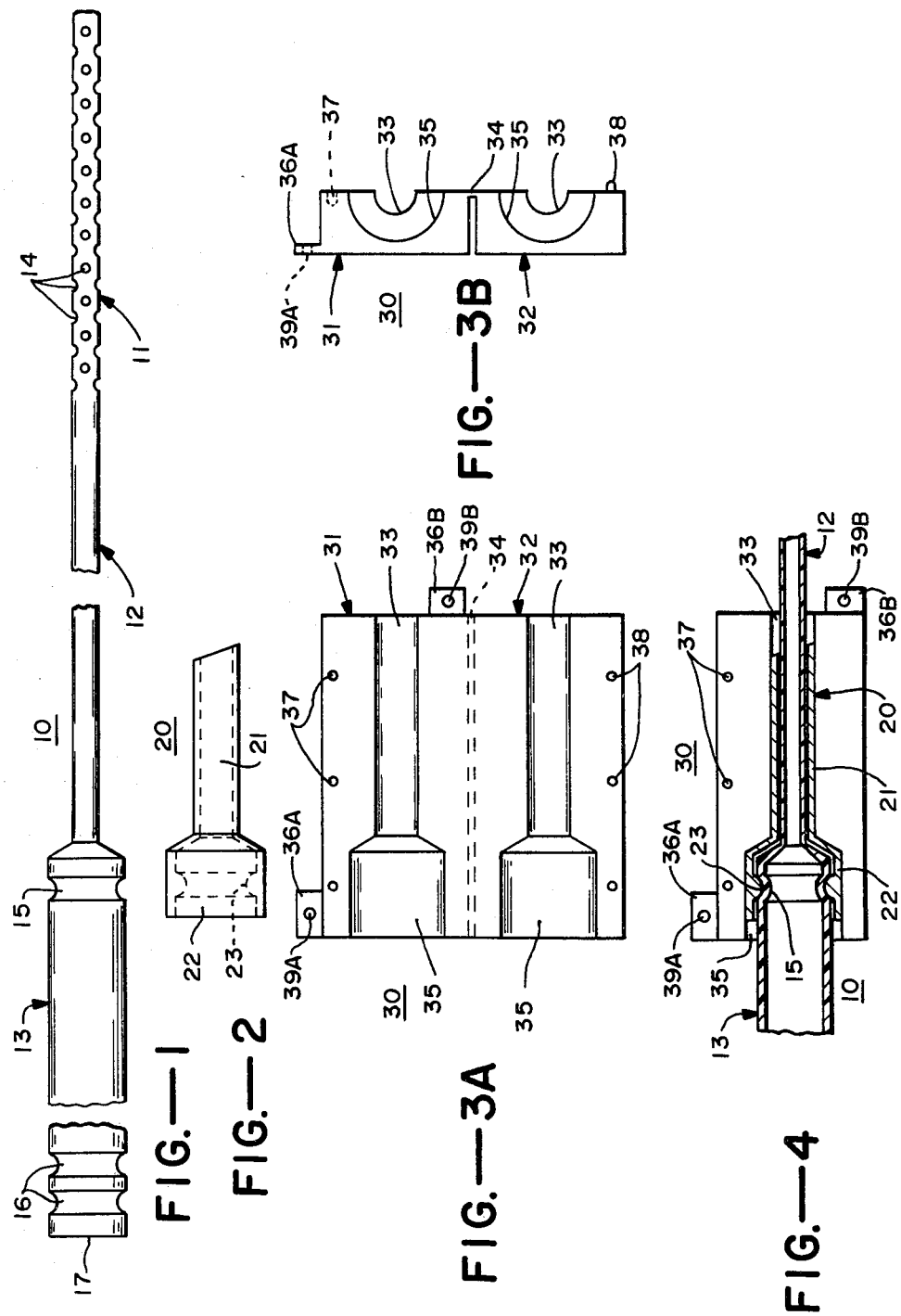

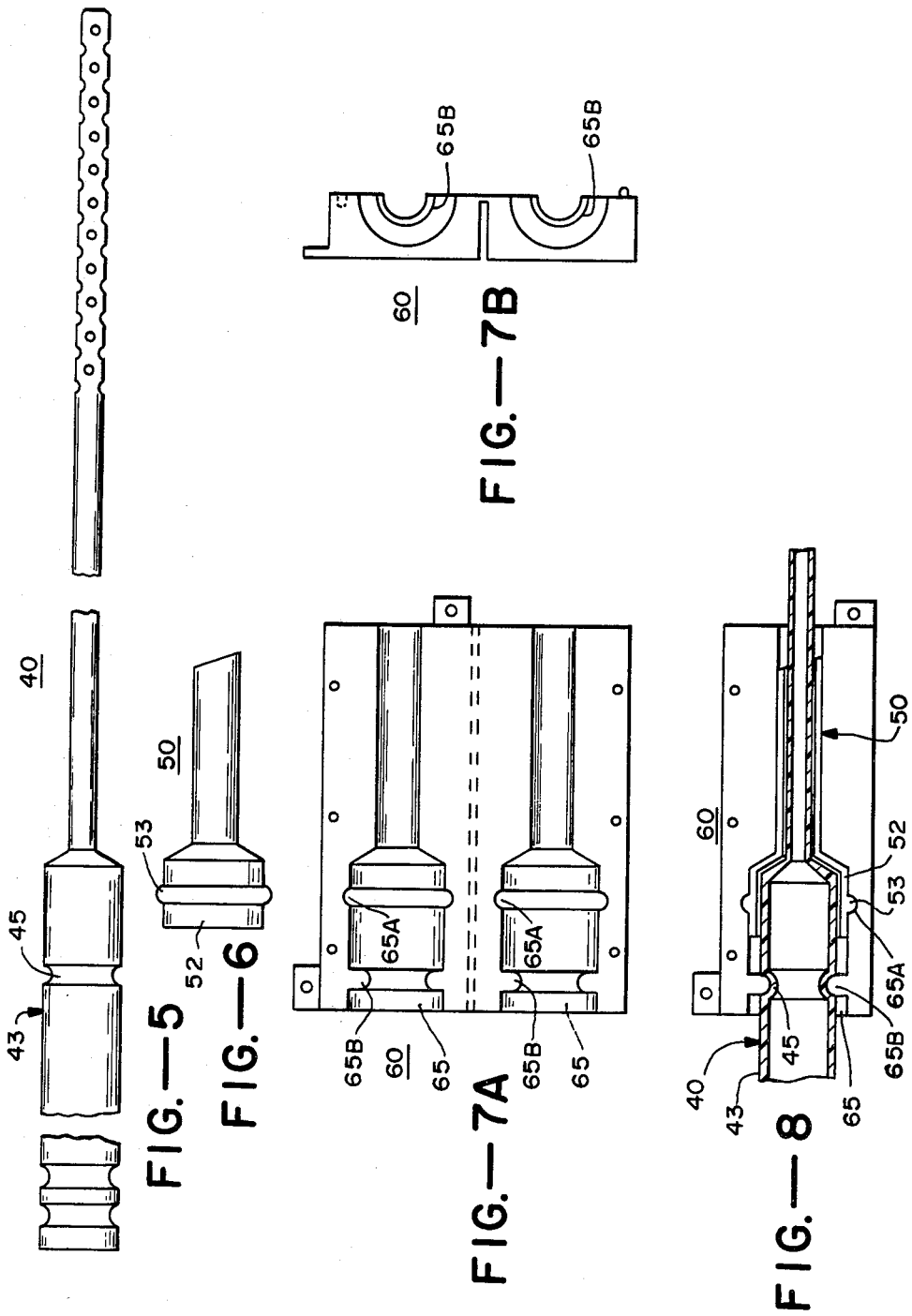

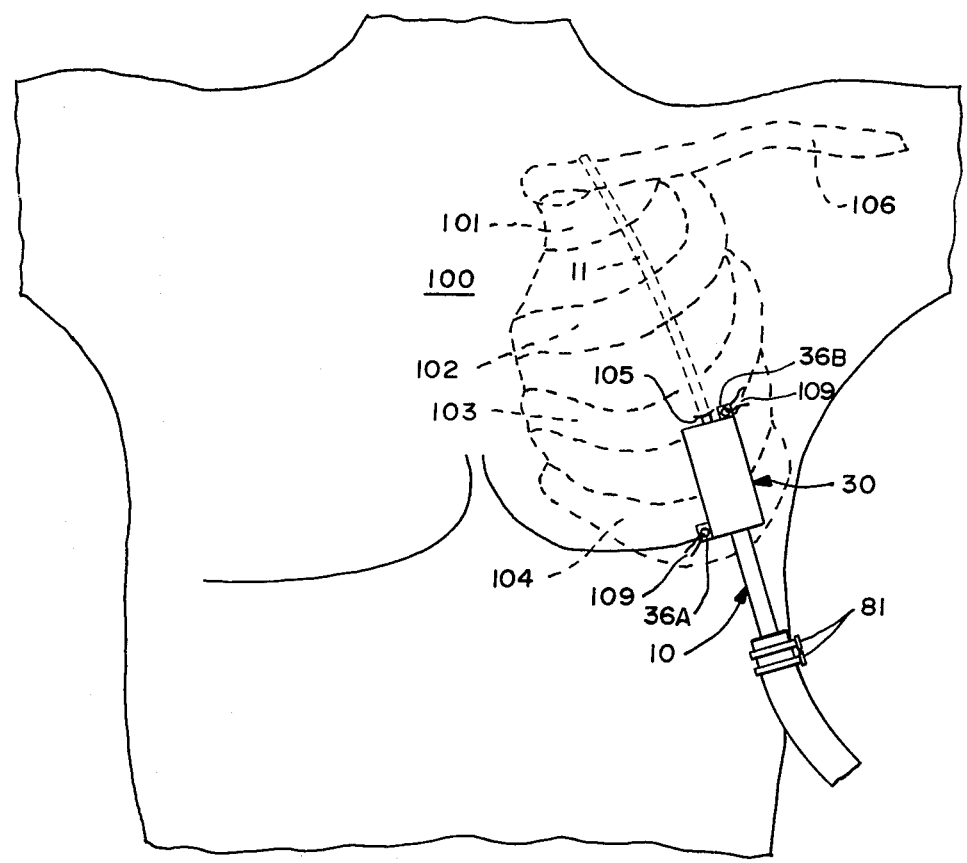
FIG.—9
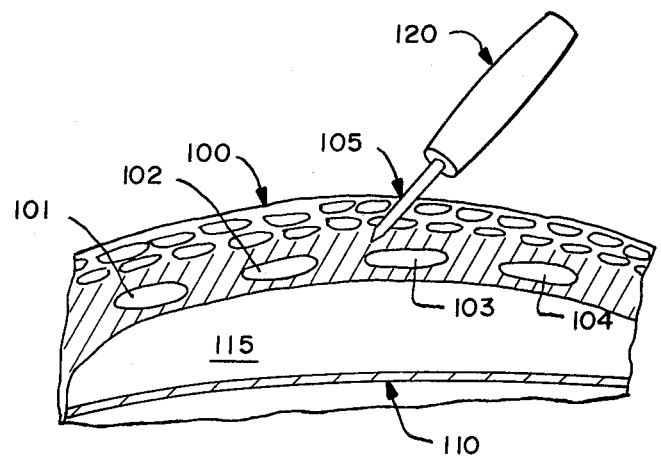
FIG.—10

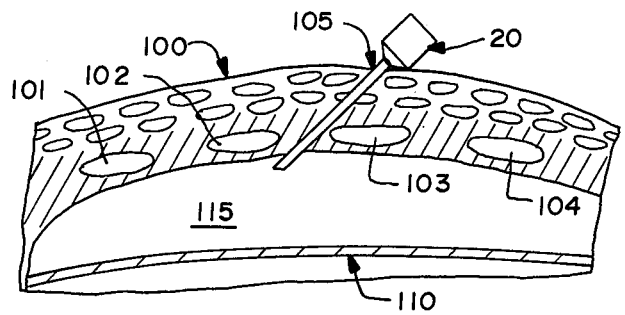
FIG.—11
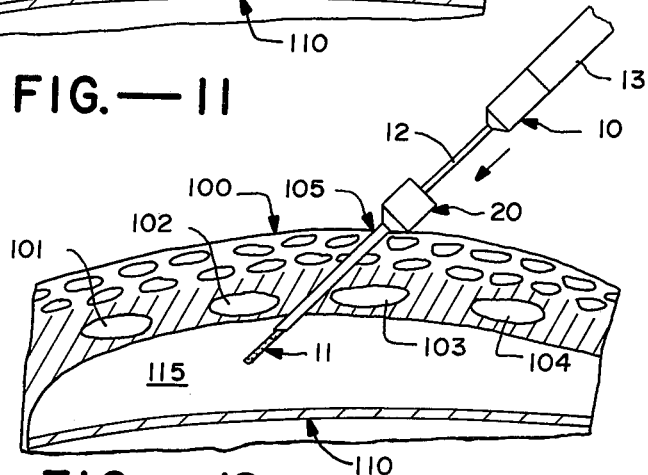
FIG.—12
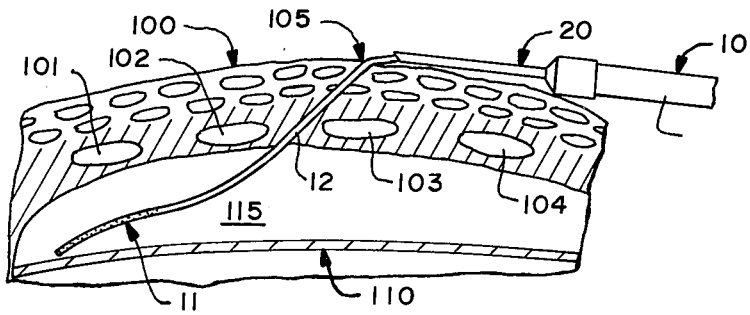
FIG.—13
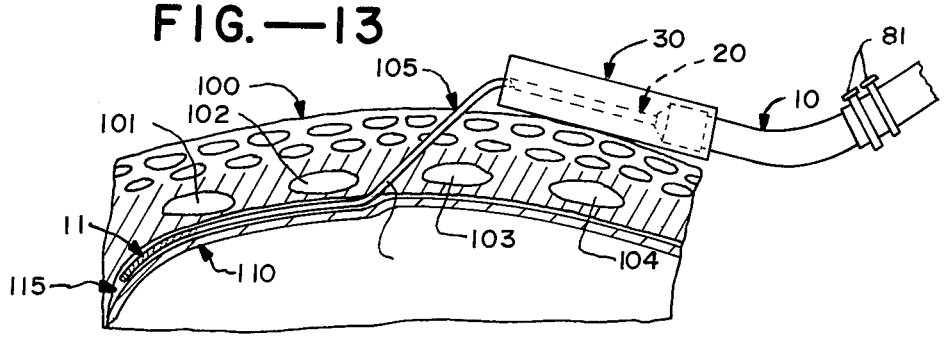
FIG.—14

APPARATUS AND METHOD FOR PERFORMING A THORACIC OPERATION

This invention relates generally to apparatus and methods for performing a medical operation and, more specifically, to apparatus and methods for performing a thoracic operation.

Pneumothorax is a condition frequently encountered in medical practice. The condition involves leakage of air from a lung of the patient which causes partial or complete collapse of the lung and thus restricts the breathing of the patient. The standard treatment for pneumothorax is the performance of a chest-tube thoracostomy. This surgical operation usually involves making an incision about one-and-one-half inches in length in the chest wall of the patient, normally between the second and third rib at the mid-clavicular line after installing a local anesthetic. Then through this incision a tunnel is made through the chest wall using a clamp. The chest wall is punctured with the clamp and spread apart so that it will accommodate a chest tube which is about one-and-one-half centimeters in diameter. The chest tube is then picked up with a clamp and pushed into the chest wall at an angle directed toward the apex of the lung. After the chest tube is fully inserted, the incision in the chest wall is sutured and the chest tube is anchored to the patient's chest wall with sutures.

While a chest tube thoracostomy is generally regarded by the medical profession as a minor surgical procedure, it is extremely painful for the patient. The entering of the clamp through the chest wall and the spreading of the chest wall to allow passage of the chest tube causes considerable pain in spite of the region having previously been anesthetized. The degree of pain involved in a thoracostomy is such that, in some instances, a patient who has previously undergone such an operation will refuse to have the operation repeated and will instead choose to undergo a thoracotomy and pleurodesis. Thoracotomy and pleurodesis is a much more radical surgical procedure which is performed under a general anesthetic and involves making a large incision in the chest wall, usually right below the fifth rib, spreading the chest wall apart and then removing the internal covering of the chest wall so that, afterwards, scarring will be formed between the lung and the chest wall to seal up any air leaks that might occur from the lung. In view of the painful nature of a chest-tube thoracostomy, it would be beneficial to have available a more benign operation for the treatment of pneumothorax.

In accordance with one aspect of this invention, a kit of instruments adapted for use in performing a percutaneous thoracic operation on a patient is provided. In accordance with another aspect of this invention a method for performing a percutaneous thoracic operation on a patient is provided.

In accordance with this invention the kit of instruments includes a hollow needle having one end adapted to be inserted into the patient through the chest wall, between a pair of ribs and into the pleural cavity, and a hollow tube having a distal portion and a proximal portion with the proximal portion having at least one aperture therein and being adapted to be inserted through the hollow needle into the pleural cavity of the patient. The distal portion of the hollow tube has at least one aperture and is adapted to be connected to a means for evacuating fluid (air or liquid) from the pleural cavity of the patient through the hollow tube.

In one embodiment of the kit, a distal portion of the hollow needle is adapted to receive a section of the distal portion of the hollow tube and a first means provided on the distal portion of the hollow needle and a second means provided on the section of the hollow tube are adapted to lock the needle and tube together.

A preferred embodiment of the kit further includes a cover means adapted to be mounted over at least a portion of the needle and a portion of the hollow tube after the needle has been withdrawn from the chest wall of the patient with the cover means including anchor means adapted to be fastened to the skin of the chest of the patient with sutures to maintain the cover means, the needle and the tube in a fixed position on the patient.

An alternative embodiment of the kit includes a cover means adapted to be mounted over at least a portion of the needle and a portion of the tube extending therethrough, after the needle has been withdrawn from the chest of the patient, and means formed on each of the cover means, the needle and the tube are adapted to lock the cover means, the needle and the tube together. In this embodiment the cover means also includes anchor means adapted to be fastened to the skin of the chest of the patient with sutures to maintain the cover means, the needle and the tube in a fixed position on the patient.

In accordance with this invention, a method for performing a percutaneous thoracic operation is provided which involves first inserting a hollow needle into the chest wall of the patient between a pair of ribs until one end thereof extends into the pleural cavity. Then, through the hollow needle is partially inserted a hollow tube having a proximal portion with at least one aperture therein extending into the pleural cavity and a distal portion having at least one aperture therein remaining outside the patient. The final step involves evacuating fluid (air or liquid) from the pleural cavity of the patient through the hollow tube.

Preferably, prior to inserting the hollow needle, a step of penetrating the skin of the patient with a surgical blade is performed to enable easier insertion of the hollow needle. It is also preferable to only partially advance the proximal end of the hollow tube (or pneumotube) toward the apex of the chest cavity before withdrawing the hollow needle from the chest wall and then fully advancing the proximal end of the pneumotube to the apex of the chest cavity. Finally, a preferred method according to this invention includes the further steps of assembling a cover with suture anchors thereon over the needle and pneumotube and then sewing the cover to the skin of the chest wall of the patient with sutures at the suture anchors to maintain the cover, the needle and the pneumotube in position on the patient.

The kit of instruments and method provided in accordance with this invention enables the performance of a percutaneous thoracic operation for the relief of pneumothorax. This percutaneous operation has a number of distinct advantages over a chest tube thoracostomy. Because the procedure involves percutaneous insertion of a pneumotube, it is not a surgical procedure and thus should be able to be performed by all medical doctors. The risks and complications involved in this procedure are less than a standard thoracostomy. The insertion of the needle and the pneumotube through the needle causes considerably less patient discomfort and produces virtually no scar after the small incision in the chest wall has healed. Finally, the operation should be less costly to the patient since the attendance of a surgeon is not required.

Other features and advantages of this invention will be apparent from the consideration of the following detailed description of alternative embodiments of the apparatus and methods in conjunction with the accompanying drawings.

FIG. 1 is an elevational view of one embodiment of a pneumotube in accordance with this invention.

FIG. 2 is an elevational view of one embodiment of a hollow needle in accordance with this invention.

FIG. 3A is an elevational view and FIG. 3B is a side view of one embodiment of a cover assembly in accordance with this invention.

FIG. 4 is a fragmented cross-sectional view of an assembly of the pneumotube shown in FIG. 1, the hollow needle shown in FIG. 2 and the cover assembly shown in FIGS. 3A and 3B.

FIG. 5 is an elevational view of an alternative embodiment of a pneumotube in accordance with this invention.

FIG. 6 is an elevational view of an alternative embodiment of a hollow needle in accordance with this invention.

FIG. 7A is an elevational view and FIG. 7B is an end view of an alternative version of a cover assembly in accordance with this invention.

FIG. 8 is a fragmented cross-sectional view of the pneumotube of FIG. 5, the needle of FIG. 6 and the cover assembly of FIGS. 7A and 7B assembled together.

FIG. 9 depicts the respective positions of a pneumotube, needle, and cover assembly after a percutaneous pneumotube insertion operation has been performed on a patient.

FIGS. 10 to 14 are fragmented cross-sectional views of the chest of a patient which illustrates sequential steps in performing a thoracic operation in accordance with this invention.

FIG. 1 depicts a pneumotube 10 in accordance with one embodiment of this invention. Pneumotube 10 comprises a proximal portion 11, an intermediate portion 12 and a distal portion 13. The proximal portion 11 and intermediate portion 12 comprise a hollow tube preferably formed to an external diameter of about 5 millimeters. Intermediate portion 12 is preferably about thirteen centimeters long and has no apertures therein. Proximal portion 11 is preferably about seven centimeters long and has a plurality of rows of small apertures 14 formed therein. Apertures 14 are conveniently formed about two millimeters in diameter and preferably three or four rows of such apertures are provided in proximal portion 11. The size and arrangement of apertures 14 are preferably selected in accordance with the wall thickness and material of proximal portion 11 such that that portion in the pneumotube will have sufficient rigidity to be able to be advanced directionally in the thoracic cavity of a patient but also have sufficient flexibility to conform to the chest wall as the patient's lung expands.

Distal portion 13 of pneumotube 10 is preferably formed to a somewhat larger diameter than intermediate portion 12 and proximal portion 11. As shown in FIG. 1 a front section of distal portion 13 has a reduced diameter portion 15 formed therein which serves as part of a locking means. In addition a pair of reduced diameter portions 16 are formed at the rear section of distal portion 13 for convenience of connecting and clamping that end of the pneumotube to another tube leading to a pleurovac or a Heimlich valve. The rear end of pneumotube 10 has an opening 17 therein so that air can be evacuated from the pneumotube.

Pneumotube 10 is preferably formed of a silastic compound with a smooth external surface. The use of silastic is preferable for its compatibility with the human body and its ability to withstand sterilization. The smooth exterior is preferable for ease in inserting proximal portion 11 and intermediate portion 12 thereof through a hollow needle.

FIG. 2 depicts a hollow needle 20 in accordance with one embodiment of this invention. Needle 20 includes a proximal portion 21 comprising a hollow, thin wall metal cylinder having an internal diameter of about six millimeters to accommodate the passage of the proximal and intermediate portions of pneumotube 10 shown in FIG. 1. Distal portion 22 of needle 20 preferably has, as shown, a larger internal diameter with a circumferential rib 23 formed on an interior surface thereof. As shown in FIG. 4 the front end of the distal portion 13 of pneumotube 10 is adapted to be received in the distal portion 22 of needle 20 with the rib 23 on needle 20 engaging the reduced diameter section 15 on pneumotube 10. In this fashion the pneumotube 10 and needle 20 may be locked together. Needle 20 is preferably formed of surgical stainless steel or aluminum and the leading or front end thereof is sharpened to permit easier passage through body tissue.

FIGS. 3A and 3B show a cover assembly 30 which is adapted to be mounted over needle 20. Cover assembly 30 essentially comprises two half sections 31 and 32 joined together with a hinged portion 34. Each of the half sections 31 and 32 have a first semi-circular cavity 23 formed therein and adapted to receive one half of the proximal portion 21 of needle 20 shown in FIG. 2. Similarly each of the half sections 31 and 32 have a second, larger semi-circular cavity 35 in the other end thereof adapted to receive one half of distal portion 22 of needle 20 shown in FIG. 2. FIG. 4 shows the respective proximal and distal portions 21 and 22 of needle 20 received in the respective cavities 33 and 35 of one half section of cover assembly 30. A plurality of posts 38 provided on section 32 are adapted to be received in apertures 37 formed in section 31 in order to lock sections 32 and 31 together over needle 20. A pair of suture anchors 36A and 36B are formed on half section 31 with apertures 39A and 39B therethrough. As will later be seen these suture anchors 36A and 36B are adapted to enable cover assembly to be sewn to the chest wall of a patient to maintain cover assembly 30 with needle 20 and pneumotube 10 captivated therein in a fixed position on the chest wall.

FIG. 4 shows the pneumotube of FIG. 1, the needle of FIG. 2 and the cover assembly of FIGS. 3A and 3B assembled together. As shown in FIG. 4 the internal diameter of proximal portion 21 of needle 20 is slightly larger than the external diameter of proximal and intermediate portions 11 and 12 of pneumotube 10 in order that those portions of pneumotube 10 can easily be pushed through needle 20. The distal portion 22 of needle 20 accommodates the front end of the distal portion 13 of pneumotube 10 with rib 23 on needle 20 engaged in reduced diameter section 15 of pneumotube 10. Cover assembly 30 fits tightly over needle 20 such that once both half sections of cover assembly 30 have been mounted over needle 20 and snapped together, needle 20 is captured inside cover assembly 30 and cannot be removed unless cover assembly 30 is snapped apart. As will later be seen this enables these three parts to be retained in a fixed position on the chest wall of the patient when suture anchors 36A and 36B are attached to the chest wall of the patient with sutures.

FIGS. 5-8 depict alternative embodiments of a pneumotube 40, a needle 50, a cover assembly 60 and an assembly of these respective instruments. Referring to FIG. 5, it can be seen that pneumotube 40 is virtually identical in structure to pneumotube 10 depicted in FIG. 1 with the exception that the reduced diameter section 45 in distal portion 43 is formed at a different location. As shown in FIG. 8 reduced diameter portion 45 is formed at a location on distal portion 43 which will enable it to cooperate with rib 65B in cover assembly 60 to lock pneumotube 40 in position in cover assembly 60.

FIG. 6 depicts a hollow needle 50 having essentially the same structure as hollow needle 20 depicted in FIG. 1 with the exception of rib 53 formed externally on distal portion 52 of needle 50. External rib 53 is provided as an alternative to internal rib 23 in needle 20 to cooperate with an internal groove 65A in cover assembly 60 to provide a positive locking of needle 50 into position in cover assembly 60 as shown in FIG. 8.

FIGS. 7A and 7B depict a cover assembly 60 which is in most respects the same as cover assembly 30 in FIGS. 3A and 3B. However, cover assembly 60 is formed slightly longer than the cover assembly 30 and the larger cavities 65 which are adapted to receive the distal sections 52 and 43 of needle 50 and pneumotube 40, respectively, have a different internal structure. As previously mentioned, an internal groove 55A is adapted to receive an external rib 53 on needle 50 to lock needle 50 into cover assembly 60. Furthermore a rib 65B formed in channel 65 snaps into reduced diameter portion 45 on pneumotube 40. As shown in FIG. 8 the final assemblage of pneumotube 40, needle 50 and cover assembly 60 provides for the positive locking of needle 20 in position in cover assembly 60 and the separate locking of pneumotube 40 in cover assembly 60.

Having described alternative embodiments of a kit of instruments adapted for use in performing a percutaneous thoracic operation on a patient, the steps involved in performing such an operation will now be detailed. However, it will be convenient first to consider the placement of the parts of the kit on and within the patient after the operation has been completed. Referring to FIGS. 4, 9 and 14 together, it will be seen that cover assembly 30 is fastened in position on the chest 100 of the patient by sutures 109 which are placed through the skin of the chest and through suture anchors 36A and 36B. (For purposes of this description the instruments depicted in FIGS. 1 through 4 will be referred to, although it is to be understood that the alternative embodiments depicted in FIGS. 5 to 7 could be substituted.) Hollow needle 20 is captured inside cover assembly 20. Also, pneumotube 10 is locked together with needle 20. In this manner cover assembly 30, needle 20 and pneumotube 10 are captured in a fixed position on the chest 100 of the patient.

Intermediate portion 12 of pneumotube 10 extends through incision 105 in the skin of the patient's chest 100 through the chest wall and partly into the pleural cavity 115. Proximal portion 11 of pneumotube 10 is positioned completely within the pleural cavity 115 with its front end near the apex of the chest wall of the patient. Distal portion 13 of pneumotube 10 is shown connected at its rear section to a tube 80 which is preferably connected at its other end to a pleurovac to provide for the evacuation of air from the pleural cavity 115 through the apertured proximal portion 11 of pneumotube 10. Clamps 81 cooperate with grooves 16 (FIG. 1) at the rear end of pneumotube 10 to fasten tube 80 and pneumotube 10 together. As shown in FIG. 14, the lung 110 of the patient has assumed an expanded position and the patient is thus able to breathe normally.

The steps employed in performing a percutaneous pneumotube insertion are readily understood from a consideration of FIGS. 10 through 14. FIG. 10 shows a portion of a cross section of the chest of the patient. The patient's chest is generally designated by the reference numeral 100. The first four ribs of the patient are designated by the reference numerals 101 through 104, respectively. FIG. 10 shows the patient's lung 110 in a collapsed position due to the leakage of air into the thoracic cavity designated by the reference numeral 115. Prior to beginning the operation, normal procedures of prepping and draping the anterior chest wall are performed. In particular the draping is provided in a manner which exposes the clavicle and first four anterior ribs of the patient. In this case it is assumed as shown in FIG. 9, that pneumothorax has occurred in the left lung of the patient. The next step is to instill a local anesthetic starting at the inferior border of the third rib 103 at a location along the mid line of the clavicle 106 shown in FIG. 9. Instilling of the local anesthetic is continued to anesthetize a tunnel subcutaneously to and above the superior border of the third rib 103, continuing through the second intercostal space above the third rib until the pleural cavity 115 is reached. As the pleural cavity is reached, the withdrawal of air into the anesthetic needle will be noted.

After the anesthetic has taken effect, it is preferable to to penetrate the skin of the chest wall of the patient with a number eleven surgical blade at the mid-clavicular line of the inferior border of the third rib where the hollow needle is to be inserted. This step in the procedure is depicted in FIG. 10 which shows a surgical blade 120 penetrating the skin of the patient's chest 100 to form a small incision 105 about one-half centimeter in length.

The next step of the procedure is depicted in FIG. 11. Needle 20 is inserted through incision 105 and advanced through the anesthetized tract to enter the pleural cavity 115 above the third rib 103 and in the direction of the apex of the chest cavity. Because of the incision formed in the chest wall, needle 20 is readily advanced through the anesthetized tract of the patient's chest wall with little or no discomfort to the patient.

The next step of the procedure continuous with insertion of proximal portion 11 of pneumotube 10 into the thoracic cavity 115 through needle 20 as depicted in FIG. 12. With needle 20 extending through the patient's chest wall the proximal portion 11 and a part of intermediate portion 12 of pneumotube 10 are easily advanced into the thoracic cavity 115. The end of proximal portion 11 is advanced in the direction of the apex of the patient's chest cavity until the front tip thereof is almost at the apex.

The next step, as shown in FIG. 13 is to withdraw the needle 20 out of the chest wall of the patient. Then the pneumotube 10 is fully advanced to the apex of the patient's chest cavity. As shown in FIG. 13 the intermediate portion 12 of pneumotube 10 now extends through the chest wall of the patient and proximal portion 11 is contained completely within the thoracic cavity 115. Needle 20 has been withdrawn out of the chest wall and pneumotube 10 has been advanced through needle 20 until the respective locking means on needle 20 and pneumotube 10 have been engaged to lock the two together.

The procedure continues with the step of mounting cover assembly 30 over needle 20 and pneumotube 10 as shown in FIG. 14. Once cover assembly 30 is in place, it is sewn to the chest wall of the patient with sutures 109 after instilling a local anesthetic at the skin positions adjacent the suture anchors 36A and 36B on cover assembly 30.

Finally, the distal end of the pneumotube 110 is connected to an underwater seal and suction of a pleurovac or a Heimlich value to evacuate air from the thoracic cavity through pneumotube 10. This permits the lung 110 of the patient to expand substantially to its normal position within thoracic cavity 115 and enables the patient to breathe normally. Thereafter, the patient's chest is X-rayed to verify the position of the pneumotube in the chest cavity and the expansion of the patient's lung.

Typically pneumotube 10 will be left in the patient for up to one week's time, during which the patient's lung normally will heal itself to eliminate leakage of air into the thoracic cavity. At this time the the sutures which hold the cover assembly 30 in place on the patient's chest wall may be removed and the pneumotube 10 may be retracted out of the patient's chest. The small incision 105 in the patient's chest may then be covered with a small adhesive bandage and will heal rapidly without any noticeable scar.

This invention has been described above in connection with two alternative embodiments of a kit of instruments adapted to be utilized in performing a thoracic operation involving the percutaneous insertion of a pneumotube. A preferred method for performing such an operation using these instruments has also been detailed. It should be apparent to those of skill in this art, however, that numerous modifications could be made in the instruments and in the method for performing the operation without departing from the general principles of this invention. For example, while the use of a cover means such as depicted in FIGS. 3A and 3B or FIGS. 7A and 7B is preferred, it will be appreciated that it would be possible to perform the operation according to this invention without the use of a cover assembly by simply sewing or taping the pneumotube, locked in position in needle 20, to the chest wall of the patient. Needle 20 could be wrapped with adhesive tape in this alternative approach to protecting the patient's skin from the sharp end of the needle. It will also be appreciated that many other approaches could be used to lock the pneumotube and needle together and to captivate both in a cover assembly.

It should also be understood that, while the kit of instruments and the operative steps described above are directed to evacuating air for relieving a condition of pneumothorax in a patient, the kit may also be utilized with similar operative steps to evacuate liquid from the pleural cavity of a patient.

It should thus be apparent that numerous modifications can be made in the apparatus and method described above without departing from the scope of this invention.

What is claimed is:

1. In a kit of instruments adapted for use in performing a percutaneous thoracic operation on a patient, a hollow needle having one end adapted to be inserted into said patient through the chest wall, between a pair of ribs, and into the pleural cavity; and a hollow tube having a distal portion and a proximal portion, said proximal portion having at least one aperture therein and being adapted to be inserted through said hollow needle into said pleural cavity, said distal portion having at least one aperture therein and being adapted to be connected to means for evacuating fluid from said pleural cavity of said patient through said hollow tube, said distal portion of said hollow needle being adapted to receive a section of said distal portion of said hollow tube, and a first means carried on an interior surface of said distal portion of said hollow needle and a second means carried on an exterior surface of said section of said hollow tube being adapted to lock said hollow needle and said hollow tube together.

2. Apparatus as claimed in claim 1, further comprising a cover means adapted to be mounted over at least a portion of said needle and a portion of said tube after said needle has been withdrawn from the chest of said patient leaving said proximal portion of said tube in said pleural cavity of said patient, said cover means including anchor means adapted to be fastened to the skin of the chest of said patient with sutures to maintain said cover means, said needle and said tube in a fixed position on said patient.

3. In a kit of instruments adapted for use in performing a percutaneous thoracic operation on a patient, a hollow needle having one end adapted to be inserted into said patient through the chest wall, between a pair of ribs, and into the pleural cavity; and a hollow tube having a distal portion and a proximal portion, said proximal portion having at least one aperture therein and being adapted to be inserted through said hollow needle into said pleural cavity, said distal portion having at least one aperture therein and being adapted to be connected to means for evacuating fluid from said pleural cavity of said patient through said hollow tube, said distal portion of said hollow needle being adapted to receive a section of said distal portion of said hollow tube, and a first means carried on an interior surface of said distal portion of said hollow needle and a second means carried on an exterior surface of said section of said hollow tube being adapted to lock said hollow needle and said hollow tube together; and a cover means adapted to be mounted over at least a portion of said needle and a portion of said tube after said needle has been withdrawn from the chest of said patient leaving said proximal portion of said tube in said pleural cavity of said patient; means formed on each of said cover means, said needle and said tube adapted to lock said cover means, said needle and said tube together; and anchor means formed on said cover means adapted to be fastened to the skin of the chest of said patient with sutures to maintain said cover means, said needle and said tube in a fixed position on said patient.

4. In a kit of instruments adapted for use in performing a percutaneous thoracic operation on a patient, a hollow needle having one end adapted to be inserted into said patient through the chest wall, between a pair of ribs, and into the pleural cavity; and a hollow tube having a distal portion and a proximal portion and being adapted to be inserted through said hollow needle into said pleural cavity, said distal portion having at least one aperture therein and being adapted to be connected to means for evacuating fluid from said pleural cavity of said patient through said hollow tube, said hollow tube being formed of a silastic compound, said proximal portion of said hollow tube having a plurality of rows of small, separated apertures extending along the walls thereof, the walls of said proximal portion otherwise having sufficient rigidity to enable the end of said proximal portion to be directed toward the apex of the lung of a patient having a documented pneumothorax but having sufficient flexibility to conform to the wall of said pleural cavity as the lung of said patient expands upon evacuation of air from said pleural cavity through said tube.

5. In a kit of instruments adapted for use in performing a percutaneous thoracostomy on a patient having a documented pneumothorax, a hollow metal needle adapted to be inserted into said patient through the chest wall between a pair of ribs and into the pleural cavity; and a hollow rubber pneumotube having a proximal portion and a distal portion, said proximal portion having at least one aperture therein and being adapted to be inserted through said hollow needle into the thoracic cavity of said patient, said proximal portion having at least one aperture therein and being adapted to be connected to means for evacuating air from said thoracic cavity through said pneumotube; said distal portion of said pneumotube having a larger diameter than said proximal portion thereof, said hollow needle having an enlarged distal end portion adapted to receive a front section of said distal portion of said pneumotube, and means formed on an interior surface of said distal portion of said needle and means formed on an exterior portion of said front section of said pneumotube being adapted to lock said needle and said pneumotube together.

6. Apparatus as claimed in claim 5, further comprising a cover means adapted to be mounted over at least a portion of said needle and a portion of said pneumotube after said needle has been withdrawn from the chest of said patient leaving said proximal portion of said pneumotube in said thoracic cavity, said cover means including anchor means adapted to be sutured to the skin of the chest of said patient with sutures to maintain said cover means, said needle and said tube in a fixed position on said patient.

7. In a kit of instruments adapted for use in performing a percutaneous thoracostomy on a patient having a documented pneumothorax, a hollow metal needle adapted to be inserted into said patient through the chest wall between a pair of ribs and into the pleural cavity; and a hollow rubber pneumotube having a proximal portion and a distal portion, said proximal portion having at least one aperture therein and being adapted to be inserted through said hollow needle into the thoracic cavity of said patient, said proximal portion having at least one aperture therein and being adapted to be connected to means for evacuating air from said thoracic cavity through said pneumotube; said distal portion of said pneumotube having a larger diameter than said proximal portion thereof, said hollow needle having an enlarged distal end portion adapted to receive a front section of said distal portion of said pneumotube, and means formed on an interior surface of said distal portion of said needle and means formed on an exterior portion of said front section of said pneumotube being adapted to lock said needle and said pneumotube together; and a cover means adapted to be mounted over at least a portion of said needle and a portion of said pneumotube after said needle has been withdrawn from the chest of said patient leaving said proximal portion of said tube in said thoracic cavity of said patient; means formed on said cover means, said needle and said tube adapted to lock said cover means, said needle and said tube together; and anchor means formed on said cover means and adapted to be fastened to the skin of the chest of said patient with sutures to maintain said cover means, said needle and said tube in a fixed position on said patient.

8. Apparatus as claimed in claim 2, 3, 6 or 7, wherein said cover means comprises a top section and a bottom section, each of said sections having semicircular shaped cavities therein adapted to receive one half of said needle, said top and bottom portions being adapted to snap together to captivate said needle with said pneumotube extending therethrough.

9. In a method for performing a percutaneous thoracostomy on a patient having a documented pneumothorax, the steps comprising:
  (a) inserting a hollow needle through the chest wall of said patient between a pair of ribs and into the thoracic cavity with the leading end of said needle generally directed toward the apex of the chest cavity;
  (b) inserting through said needle a proximal portion of a pneumotube having a plurality of apertures therein;
  (c) partially advancing the end of said proximal portion of said pneumotubes toward the apex of the chest cavity;
  (d) withdrawing said hollow needle from said patient's chest;
  (e) fully advancing the proximal end of said pneumotube to the apex of the patient's chest cavity; and
  (f) evacuating air from said patient's thoracic cavity through said pneumotube to enable said patient's lung to expand within said thoracic cavity.

10. The method of claim 9, wherein a step prior to inserting said hollow needle comprises penetrating the skin of the patient with a surgical blade to enable easier insertion of said needle.

11. The method claimed in claim 9 wherein the steps after removing said needle from the chest wall of the patient comprise assembling a cover having at least two suture anchors thereon over the needle and pneumotube and sewing the cover to the skin of the chest of the patient with sutures at said two anchors to maintain said cover, said needle and said pneumotube in position on said patient.

12. In a method for performing a percutaneous thoracostomy on a patient having a documented pneumothorax, the steps comprising:
  (a) instilling a local anasthetic at the inferior border of the third rib at the mid-clavicular line to anesthetize a tunnel subcutaneously to and above the superior border of the third rib, through the second intercostal space above the third rib until the thoracic cavity is entered as determined by the withdrawal of air therefrom;
  (b) penetrating the skin at the mid-clavicular line of the inferior border of the third rib with a small surgical blade to form a small incision therein;
  (c) inserting a hollow needle at an angle through the incision in the direction of the apex of the chest cavity and advancing the leading edge of said needle through the anesthetized tract into the thoracic cavity above the third rib;

(d) inserting the apertured proximal end portion of a pneumotube through the needle and advancing the proximal end of said tube in the direction of the apex of the chest cavity;
(e) withdrawing the hollow needle from the chest wall just prior to the leading edge of the pneumotube reaching the apex of the chest cavity;
(f) fully advancing the proximal end of the pneumotube to the apex of the chest cavity;
(g) placing a plastic cover having suture anchors thereon over the needle and the pneumotube and sewing the plastic cover to the skin of the chest of the patient with sutures at said suture anchors to maintain the needle and the pneumotube in a fixed position on the patient;
(h) and evacuating air from the thoracic cavity of the patient through said pneumotube to allow the lung of said patient to expand.

* * * * *